United States Patent [19]

Mauclaire et al.

[11] Patent Number: 5,268,371
[45] Date of Patent: Dec. 7, 1993

[54] DERIVATIVES OF PORPHYRIN AND METALLOPORPHYRINS OPTIONALLY COUPLED TO A BIOLOGICALLY ACTIVE MOLECULE AND PHARMACEUTICAL COMPOSITION CONTAINING THEM

[75] Inventors: Laurent Mauclaire, Paris; Catherine Bedel, Lacroix St. Ouen; Michel Pereyre, Talence; Jean-Claude Saccavini, Verrieres le Buisson, all of France

[73] Assignee: CIS bio International, Saclay, France

[21] Appl. No.: 943,299

[22] Filed: Sep. 10, 1992

[30] Foreign Application Priority Data

Jan. 10, 1990 [FR] France .................... 90 00214

[51] Int. Cl.$^5$ ............ A61K 31/40; C07D 487/22
[52] U.S. Cl. ............................ 514/185; 534/10
[58] Field of Search ............... 514/185; 534/10

[56] References Cited

U.S. PATENT DOCUMENTS

| | | | |
|---|---|---|---|
| 4,614,723 | 9/1986 | Schmidt et al. | 436/536 |
| 4,783,529 | 11/1988 | Lavallee et al. | 540/145 |
| 4,851,403 | 7/1989 | Picker et al. | 514/185 |
| 4,877,872 | 10/1989 | Morgan et al. | 514/185 |
| 5,109,016 | 4/1992 | Dixon et al. | 514/185 |

FOREIGN PATENT DOCUMENTS

| | | |
|---|---|---|
| 127797 | 12/1984 | European Pat. Off. |
| 186962 | 7/1986 | European Pat. Off. |
| 329363 | 2/1988 | European Pat. Off. |
| 345171 | 12/1989 | European Pat. Off. |

OTHER PUBLICATIONS

Journal of Immunological Methods, vol. 105 (1987), pp. 153-164 Roberts, J. C. et al., "Prep and Characterization . . . ".
Bulletin of the Chemical Society of Japan, vol. 54 (1981), pp. 3879-3880, Takagi S. et al, "Synthesis of Amphiphilic Porphyrins . . . ".
Patent Abstracts of Japan, vol. 7, No. 277 1983, (C-199) (1422).

*Primary Examiner*—C. Warren Ivy
*Assistant Examiner*—James H. Turnipseed
*Attorney, Agent, or Firm*—Michael N. Meller

[57] ABSTRACT

The present invention relates to metallized porphyrin derivatives having the formula:

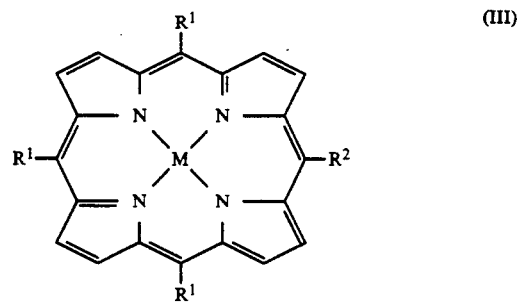

(III)

wherein the R and M variables are as defined in the specification. Said porphyrin derivatives having uses as antitumor agents, diagnostics agents, or in therapy.

11 Claims, No Drawings

DERIVATIVES OF PORPHYRIN AND METALLOPORPHYRINS OPTIONALLY COUPLED TO A BIOLOGICALLY ACTIVE MOLECULE AND PHARMACEUTICAL COMPOSITION CONTAINING THEM

This is a continuation-in-part of PCT application FR91/00010 filed Jan. 9, 1991.

The present invention relates to an optionally metallized porphyrin derivative, which can be coupled to a biologically active molecule.

More specifically, it relates to porphyrin derivatives usable in the pharmaceutical field, either as antitumour agents, or diagnostic agents, or in therapy, particularly when they incorporate a radioactive metal.

The use of compounds labelled by a radioactive element as a diagnostic or therapeutic agent has become wide-spread in analytical laboratories and hospitals, where these labelled compounds are used either for scintiscanning, or for the punctiform irradiation of a malign centre.

For these uses, it is necessary to obtain a stable bond between the radioactive element and the compound, which is difficult to obtain with most radioactive elements. Moreover, up to now radioactive iodine has been mainly used and this can be directly fixed to numerous active substances. Use has also been made for this purpose of carbon 11, tritium and phosphorus 32. However the in vivo instability of certain of these radioactive elements has led to a new approach for producing labelled compounds.

Thus, in order to be able to use metals and other elements, certain labelling operations have been carried out by chelating radioactive metallic traces. The thus formed complex can be fixed to the protein elements or to their derivatives by a covalent bond. The most widely used chelating agents are ethylene diamine tetraacetic acid (EDTA) and its derivatives, as well as diethylene triamine pentaacetic acid (DTPA).

Although these complexing agents have made it possible to obtain better results, particularly for the labelling of monoclonal antibodies, the resulting labelled products also have an in vivo instability. Thus, certain plasma proteins such as transferrin, albumin, etc. displace the metals of the EDTA and DTPA complex. Therefore the radioactive metals are encountered in the flowing blood and disturb the scintigraphic analysis.

The use of other chelating agents has also been considered.

Porphyrins are compounds having a tetrapyrrolic cyclic structure, which are widespread in all animals, which inter alia exist in the form of metalloporphyrin complexes essentially with iron and magnesium. Certain of these porphyrins have a physiological activity, particularly a tumor tropism, as well as photosensitizing properties which can be used for diagnosis or therapy, as described in EP-A-210 351.

The porphyrins used in EP-A-210 351 are substituted derivatives of porphine, which have at least three carboxylic acid groups. These porphyrins have an affinity for tumour cells and when exposed to an appropriate radiation, they emit light, which makes it possible to detect the presence, the position and the size of a tumour. On irradiating the tumour with a light having an appropriate wavelength and intensity, the porphyrin is activated and exerts a destructive action on the tumour cells.

However, the tumour tropism of said porphyrins is not exclusive and a non-negligible concentration thereof occurs in all tissues, particularly in the liver, as stated in EP-A-322 198. Therefor in the case of a use for the destruction of tumour cells, irradiation also leads to a destruction of healthy tissues. Moreover, certain porphyrin compounds have a significant toxic effect in high concentrations on the nervous motility, as described by A. A. F. Sima et al in Can. J. Neurol. Sci., 8, pp. 105–114, 1981.

In order to obtain an exclusive affinity of porphyrins for tumour cells, consideration has been given to the coupling of the porphyrins to specific antibodies of said tumour cells, as is described by J. C. Roberts et al in J. Immunol. Methods, 105, 153, 1987 and in U.S. Pat. No. 4,783,529.

According to these documents, said coupling is obtained by reacting non-metallized porphyrin with a benzyl diphenyl sulphonium compound, then conjugating it with an antibody and finally carrying out metallization by a radioactive element such as $^{64}$Cu, $^{23}$Ni and $^{57}$Co. However, this preparation procedure cannot be used with all porphyrins, because it is more particularly limited to those having carboxylic groups. Moreover, the coupling must be carried out in the presence of an organic cosolvent due to the low hydrosolubility of the porphyrin derivative and the subsequent metallization can only be envisaged with metals of small size such as copper, zinc and nickel.

It would also be very interesting to have porphyrin derivatives, which can be metallized by any random metal and which have a better hydrosolubility, in order to be able to carry out their coupling with biologically active molecules in aqueous solution.

It is known that certain substituted porphyrins can be soluble in water, as is described in EP-A-322 198 and EP-A-186 982. In EP-A-322 198, the hydrosolubility is obtained by converting a pheophorbide into its ethylene diamine hydrochloride. In EP-A-186 982, the hydrosolubility is obtained by the presence of substituents constituted by sulphonate, hydroxyamino or sulphydryl groups.

However, in these two documents, the porphyrins are not suitable for a coupling with biologically active molecules and a radioactive element.

The present invention specifically relates to novel hydrosoluble porphyrin derivatives on which can be fixed very numerous radioactive metals and which easily be coupled to a biological active molecule such as an antibody.

According to the invention, the porphyrin derivative complies with the formula:

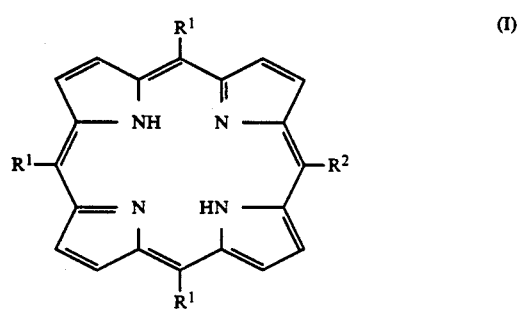

in which the $R^1$ represents a pyridyl radical and $R^2$ a radical chosen from among radicals complying the formulas:

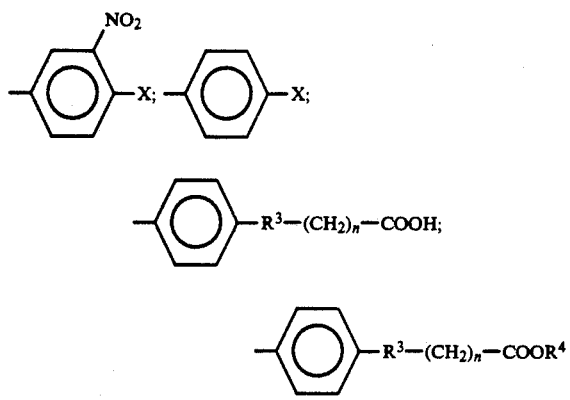

in which X represents F, Cl or Br, $R^3$ is a single bond, S or O, n is an integer from 1 to 7 and $R^4$ is a $C_1$ to $C_4$ alkyl radical, a benzyl radical or the radical of formula:

in which $R^5$ is chosen from among F, Cl, Br, I, $NO_2$ and the radical of formula $SR^6$, in which $R^6$ is a $C_1$ to $C_4$ alkyl radical, p is equal to 1 when $R^5$ represents $NO_2$ or $SR^6$, p is equal to 4 or 5 when $R^5$ represents F, Cl, Br or I and $R^5$ is in the ortho or para position when p is equal to 1.

Preferably $R^4$ and $R^6$ are ethyl or methyl radicals.

The invention also relates to the pyridylium salts of the derivative of formula (I). These pyridylium salts can comply with the formula:

(II)

in which $R^2$ has the meaning given hereinbefore, $R^7$ is a $C_1$ to $C_4$ alkyl radical and $A^-$ is an anion chosen from among $Cl^-$, $Br^-$ and $I^-$. Preferably $A^-$ is $Cl^-$ and $R^7$ is the ethyl or methyl radical.

In the porphyrin derivatives according to the invention, the pyridyl radical $R^1$ can be attached to the porphine nucleus by the carbon atom in the 2, 3 or 4 position with respect to the N of the pyridyl nucleus.

The porphyrin derivatives according to the invention can easily be metallized. In addition, the invention relates to the porphyrin derivative complying with formula:

(III)

in which the $R^1$ represent a pyridyl radical and $R^2$ a radical chosen from among radicals complying with the formulas:

in which X represents F, Cl or Br, $R^3$ is a single bond, S or O, n is an integer from 1 to 7 and $R^4$ is a $C_1$ to $C_4$ alkyl radical, a benzyl radical or the radical of formula:

in which $R^5$ is chosen from among F, CL, Br, I, $NO_2$ and the radical of formula $SR^6$, in which $R^6$ is a $C_1$ to $C_4$ alkyl radical, p is equal to 1 when $R^5$ represents $NO_2$ or $SR^6$, p is equal to 4 or 5 when $R^5$ represents F, CL, Br or I, $R^5$ is in the ortho or para position when p is equal to 1, and M is a metal; and the pyridilium salts of said derivative of formula (III).

When this derivative is in the form of the pyridilium salt, it e.g. complies with the formula:

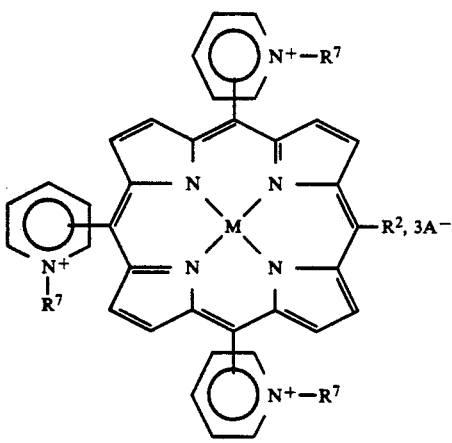
(IV)

in which $R^2$ has the meaning given hereinbefore, $R^7$ is a $C_1$ to $C_4$ alkyl radical, A is an anion chosen from among $CL^-$, $Br^-$ and $I^-$ and M is a metal. In this case, as hereinbefore, $A^-$ preferably represents $CL^-$ and $R^7$ is the ethyl or methyl radical.

In these metallized derivatives, the metal M is preferably radioactive and it can be both a metal of small size such as Cu, Zn and Ni, or a heavy metal, e.g. In, Gd, Y, Re, Tc, Sn and Ga, whose radioactive isotopes have advantageous properties for therapy or diagnosis and which have not hitherto been used in metallized porphyrin derivatives.

The radioactive metal can in particular be indium 111, technetium 99 m, rhenium 186 or rhenium 188.

Therefore the porphyrin derivatives according to the invention are of great interest for use in medicine, particularly those in which M is a metal other than Zn, Cu and Ni.

Thus, the presence of the substituent $R^2$ gives them the property of being covalently bondable to biologically active molecules such as antibodies. This is due to the presence of a halogen, a COOH group, or an activated ester group on the substituent $R^2$, which makes it possible to react the porphyrin with the amine, carboxylic, alcohol or thiol functions of the amino acid residues and glycoside residues of the proteins. The halogen can react with the amino functions of the side chains of lysines and the imidazole nucleus of histidines, as well as with the alcohol and thiol functions of serines, tyrosines and cysteines. The COOH and $COOR^4$ groups can react with the amino functions of lysines, the thiol functions of cysteines and the hydroxyl of serines and particularly tyrosines.

Moreover, it is possible to obtain with the derivatives according to the invention the desired properties of solubility in water by quaternizing the pyridyl groups to form the corresponding pyridylium salts.

Thus, the porphyrin derivatives according to the invention are soluble in water, can be metallized by a radioactive element and also have a substituent able to react with a biologically active molecule such as an antibody.

According to the invention, $R^2$ can represent the different groups described hereinbefore.

However, when the derivative according to the invention has to be coupled to a biologically active molecule, $R^2$ cannot represent a radical having an ester group if the latter is not activated.

Moreover, for said use, when $R^2$ represents the radical of formula:

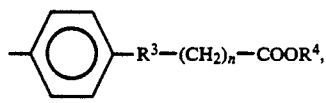

$R^4$ represents

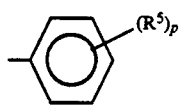

with $R^5$ and p having the meanings given hereinbefore.

When $R^2$ represents

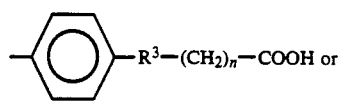

or

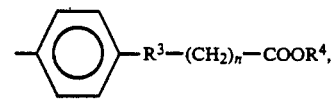

$R^3$ can represent O, S or a single bond.

As examples of such $R^2$, reference can be made to the radical of formula:

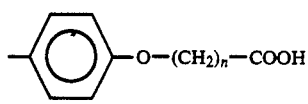

in which n is an integer from 1 to 7, and the radical of formula:

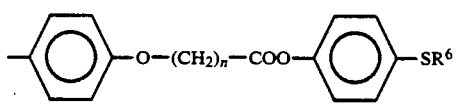

in which n is an integer from 1 to 7 and $R^6$ is the methyl or ethyl radical.

The invention also relates to a conjugate compound of a biologically active molecule and a porphyrin derivative complying with the formulas:

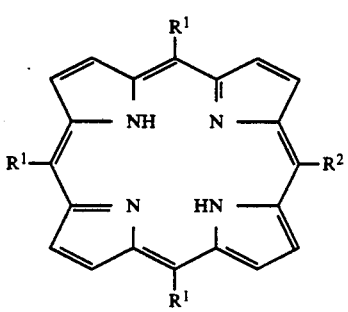
(I)

(I)

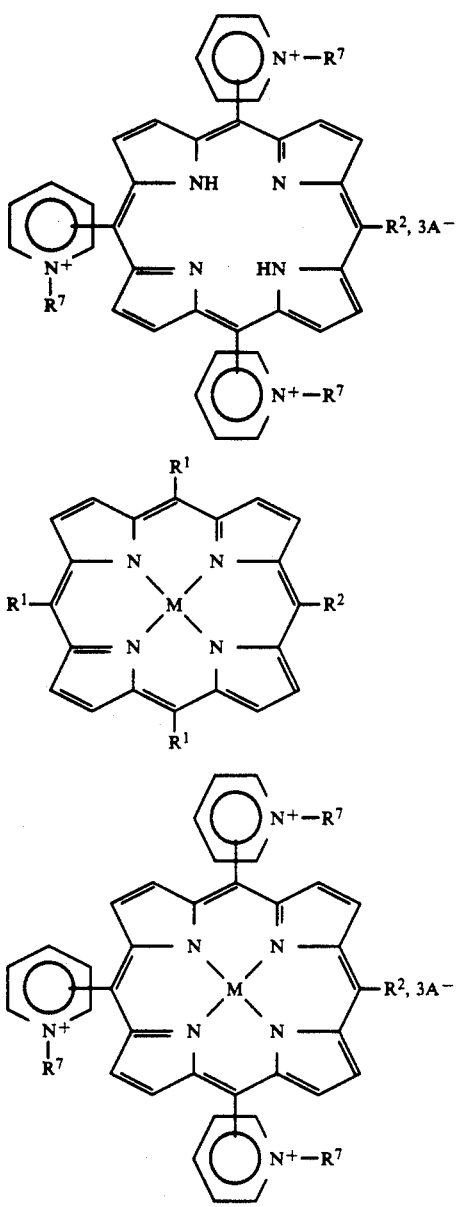

in which $R^1$, $R^2$, $R^7$, A and M have the meanings given hereinbefore, provided that $R^2$ does not represent the radical of formula:

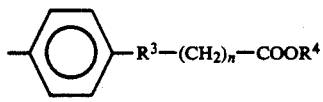

with $R^4$ representing an alkyl or benzyl radical.

The non-metallized porphyrin derivatives according to the invention can be prepared by a conventional process from pyrrole, formylpyridine and benzaldehyde in substituted form corresponding to the formula $R^2CHO$. This reaction corresponds to the following reaction diagram:

This synthesis leads to a mixture of 6 porphyrins, which are e.g. separated by chromatography to only isolate the tripyridyl derivative of formula (I) according to the invention.

According to the invention, the choice of the tripyridyl derivative of formula (I) makes it possible to avoid any subsequent crosslinking during the coupling of said derivative with a biologically active molecule and in particular to hydrosolubilize said derivative forming the corresponding pyridylium salt by quaternization of the pyridyl positions, e.g. by methylation.

The porphyrin derivatives in the form of pyridylium salt complying with formula (II) can easily be prepared from the derivative of formula (I) by a simple alkylation reaction using an alkyl halide, e.g. methyl iodide. It is then possible to transform the pyridylium iodide into chloride by passing over a chloride ion anion exchange resin.

The metallized porphyrin derivatives according to the invention can be prepared by reacting a porphyrin derivative of formula (I) or formula (II) with a solution of a salt of the metal M to be included at a temperature and for a time adequate to obtain the insertion of the metal M.

When the metal to be included is indium, e.g. radioactive indium, contacting takes place for e.g. approximately 3 h at approximately 130° C. of a porphyrin solution, preferably in the form of pyridylium salt, with a mixture of acetic and trifluoroacetic acid, to which indium trichloride is added.

When the metal to be included is yttrium, it is necessary to use higher temperatures, e.g. 250° C. for 4 h.

In the case of Sn, Ga and Tc, it is possible to e.g. use a temperature of approximately 130° C. and in the case of Gd and Re temperatures of approximately 230° C.

The fact of including the metallic element prior to the coupling of the porphyrin derivative with a biologically active molecule thus makes it possible to include any random metal, particularly heavy metals such as indium, tin, gallium, gadolinium, yttrium, rhenium and technetium, which could not be included after coupling the porphyrin to a biologically active molecule, because the temperatures and times necessary for this inclusion would lead to the destruction of said molecule.

Following said metallization, it is possible to couple the porphyrin derivative with a biologically active molecule, e.g. an antibody.

Preferably, for said coupling reaction, use is made of a porphyrin derivative in the form of a pyridylium salt for operating in an aqueous solution. Coupling can take place either directly in the case of porphyrin derivatives with $R^2$ incorporating a halogen atom or an activated ester function, or via a carbodiimide and N-hydroxysuccinimide in the case of porphyrin derivatives with $R^2$ incorporating a carboxylic group. The method used can be that described by Lavallee et al in U.S. Pat. No. 4,783,529.

The biologically active molecules which can be coupled to the porphyrin derivative according to the invention can be of different types. Examples of such molecules are antigens, antibodies, haptens, particularly antibodies and more especially monoclonal antibodies.

There are numerous applications for the porphyrin derivatives according to the invention in the medical field for diagnosis or therapy. Thus, porphyrin derivatives metallized by a radioactive element and non-metallized derivatives can e.g. be used as diagnostic or therapeutic agents for tumours.

The invention also relates to pharmaceutical compositions incorporating such derivatives, preferably in an aqueous solution.

These compositions can be administered by injection, e.g. intravenously. Following said injection, the porphyrin derivative is located in the tumour, which permits the detection or treatment of the tumor.

When the derivative is not metallized, it is possible to detect the tumour by irradiation at a wavelength such that a fluorescent light emission is obtained from said derivative. When the derivative is metallized by a radioactive element, the tumour can be detected by scintoscanning.

For therapy, when the injected derivative is not metallized, there is then an irradiation of the tumour by a light having an appropriate wavelength for activating the porphyrin derivative and for necrotizing the tumour cells.

The derivative doses used are in particular dependent on the size of the tumour and can be between 0.01 and 20 mg/kg/day.

The porphyrin derivatives, either non-metallized or metallized by a radioactive metal and coupled to a biologically active molecule can be used for the same purpose and are of particular interest, because they have a better affinity due to the presence of said biologically active molecule, e.g. a specific antibody of the tumour cells to be detected or destroyed.

Other features of the invention can be gathered from the study of the following example given in a purely illustrative and non-limitative manner.

EXAMPLE 1

Preparation of (3-nitro-4-fluorophenyl)-tripyridyl porphyrin

This derivative complies with the formula:

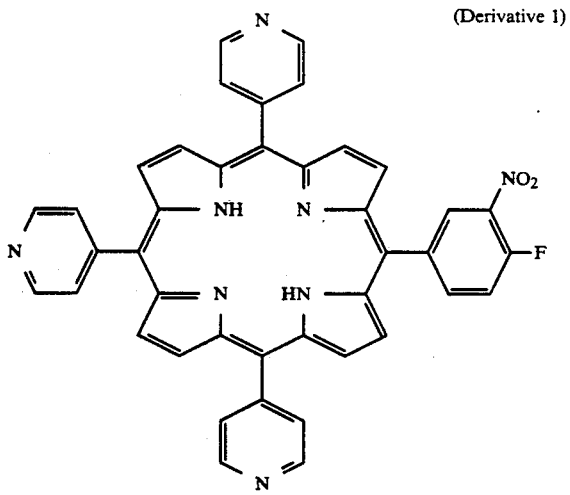
(Derivative 1)

In a round-bottomed flask containing 200 ml of propionic acid, kept under magnetic stirring, mixing takes place of $8 \cdot 10^{-2}$ mole of pyrrole, $1.33 \cdot 10^{-2}$ mole of 3-nitro-4-fluorobenzaldehyde and $6.66 \cdot 10^{-2}$ mole of 4-formyl-pyridine. After 1 hour at the reflux temperature of the acid, the solution is allowed to return to ambient temperature. The propionic acid is evaporated under reduced pressure and the mixture of porphyrins is precipitated in the minimum of dimethyl formamide (DMF).

The 6 macrocycles are then separated on a silica gel column. The expected derivative 1 is obtained by a chloroform/methanol (97:3) elution with a yield of 1.9%.

EXAMPLE 2

Preparation of (4-fluorophenyl)-tripyridyl porphyrin

This derivative complies with the formula:

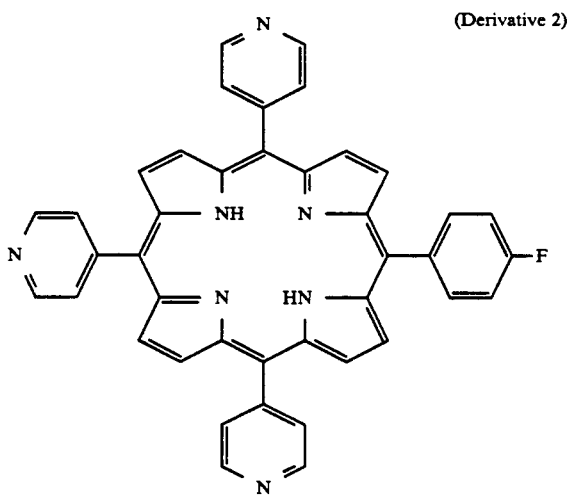
(Derivative 2)

The same operating procedure as in example 1 is adopted for preparing said porphyrin, except that use is made of $1.33 \cdot 10^{-2}$ mole of 4-fluorobenzaldehyde in place of $1.33 \cdot 10^{-2}$ mole of 3-nitro-4-fluorobenzaldehyde.

The mixture of porphyrins is precipitated with redissolving in the minimum of DMF by methanol addition. The 6 macrocyles are separated on a silica gel column and the derivative 2 is obtained by a chloroform/methanol (97:3) elution with a 2.6% yield.

EXAMPLE 3

Preparation of (4-(carboxymethoxy)-phenyl)-tripyridyl porphyrin ethyl ester

This derivative complies with formula:

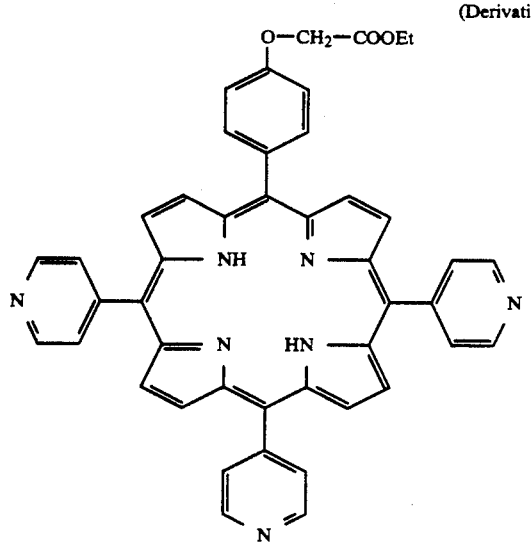

(Derivative 3)

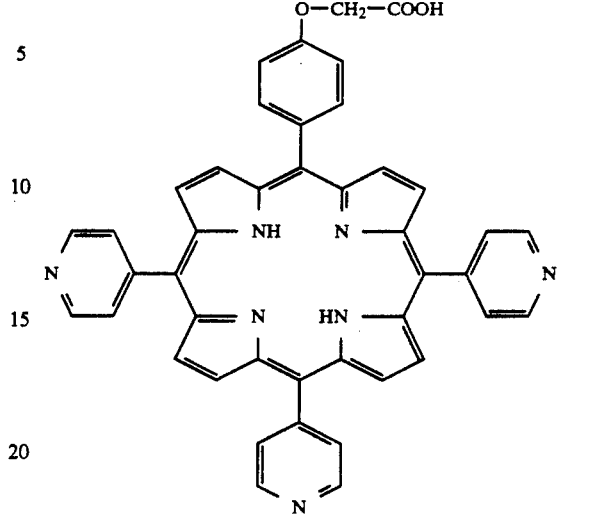

(Derivative 4)

In a round-bottomed flash addition takes place of 200 ml of propionic acid, $8 \cdot 10^{-2}$ mole of pyrrole, $1.33 \cdot 10^{-2}$ mole of 4-(carboxymethoxy)-benzaldehyde ethyl ester and $6.66 \cdot 10^{-2}$ mole of 4-formyl-pyridine. After 1 h at reflux, the reaction medium is allowed to return to ambient temperature. The propionic acid is eliminated by evaporating under reduced pressure and the six mixed porphyrins are precipitated by methanol addition after redissolving the residue in hot DMF.

The 6 macrocycles are then separated by liquid chromatography under a high preparative pressure using a silica column of length 200 mm and diameter 40 mm containing silica with an average particle size of 20 μm and a mean pore radius of 60 Å. The eluent used is a mixture of chloroform and methanol, whereof the methanol percentage varies between 0 and 3% and the flow rate is 1.2 ml/min. This gives the porphyrin derivative 3 with a yield of 5.6%.

The 4-(carboxymethoxy)-benzaldehyde ethyl ester used as the starting product in this example was prepared from 4formyl-phenoxyacetic acid by esterification in the presence of N,N'-carbonyl diimidazole.

EXAMPLE 4

Preparation of (4-(carboxymethoxy)-phenyl)-tripyridyl porphyrin

This derivative complies with the formula:

$7.22 \cdot 10^{-5}$ mole of the ethyl ester obtained in example 3 are dissolved in 50 ml of tetrahydrofuran (THF). Addition takes place of 1 ml of a solution of sodium hydroxyde-ethanol (4 g of NaOH dissolved in 5 ml of water to which are added 50 ml of ethanol). The reaction mixture is refluxed for 1 h. The solvent is evaporated and the solid residue taken up by chloroform, followed by washing with a 0.1M hydrochloric acid solution. This is followed by filtering and the solid residue is redissolved in methanol. The alcoholic solution is filtered and then evaporated to recover the expected corporate derivative 4 with a 95% yield.

EXAMPLE 5

Preparation of the 4-methyl-mercaptophenyl ester of (4-(carboxymethoxy)-phenyl)-tripyridyl porphyrin This derivative complies with the formula:

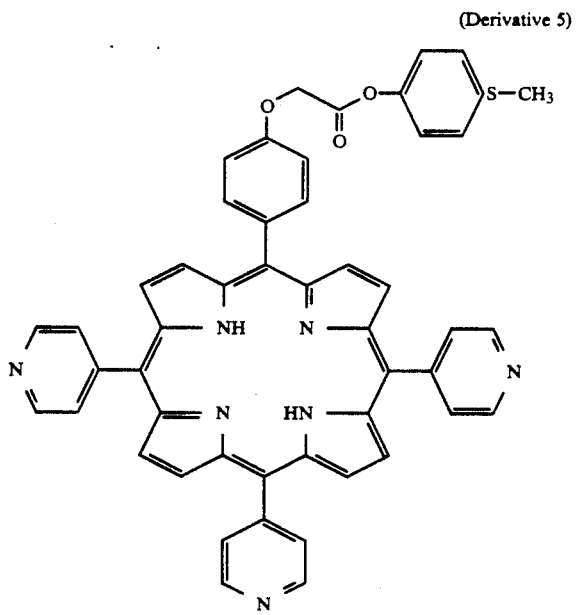

(Derivative 5)

$2.5 \cdot 10^{-5}$ mole of (4-(carboxymethoxy)-phenyl)-tripyridyl porphyrin obtained in example 4 are dissolved in 30 ml of THF and 5 ml of DMF with $2.5 \cdot 10^{-4}$ mole of dicyclocarbodiimide (DCC). When the solution is homogeneous, addition takes place at 0° C. of $5 \cdot 10^{-4}$ mole of 4-methylmercaptophenol. Following said addition, the reaction medium is returned to ambient temperature and magnetic stirring thereof is maintained for 24 h. The solvent is evaporated and the reaction medium undergoes chromatography on silica gel using as the eluent a chloroform-methanol (97:3) mixture. This gives derivative 5 with a 78% yield. It has the following physicochemical characteristics:

Visible UV spectrometry (CHCl$_3$) λ (in nm): 417; 513; 548; 588; 644.5.

$^1$H NMR (CDCl$_3$) δ(ppm): 8.94 (2H, d); 8.81 (2H, d); 8.85 (4H, s); 9.06 (6H, m); 8.17 (6H, m); 8.12 (2H, m); 7.33 (2H, m); −2.88 NH.

EXAMPLE 6

Preparation of (3-nitro-4-fluorophenyl)-trimethyl pyridylium phorphyrin

This derivative complies with formula:

of DMF and 20 ml of iodomethane. The solution is kept at 40° C. for 2h and under magnetic stirring. After this time, it is allowed to return to ambient temperature, followed by the addition of 150 ml of ethyl ether to precipitate the porphyrin. The latter is recovered by filtering, it is dried and then redissolved in methanol, after which it undergoes chromatography on a chloride ion exchange anionic resin. In this way the chloride is recovered in solution in methanol, it is evaporated to dryness and dried in vacuo. This gives the chloride, i.e. derivative 6, with a yield of 88%.

It has the following physicochemical characteristics:
Visible UV spectrometry (methanol) λ (in nm): 418; 512.5; 549.5; 589; 646.5.

$^1$H NMR (CD$_3$OD) (δ ppm): 9.05 (8H, m, L); 9.39 (6H, m); 8.93 (6H, m); 9.2 to 8.95 (2H, m) 8.71 (1H, m); −2.92 (NH).

EXAMPLE 7

Preparation of (4-fluorophenyl)-trimethyl pyridylium porphyrin chloride

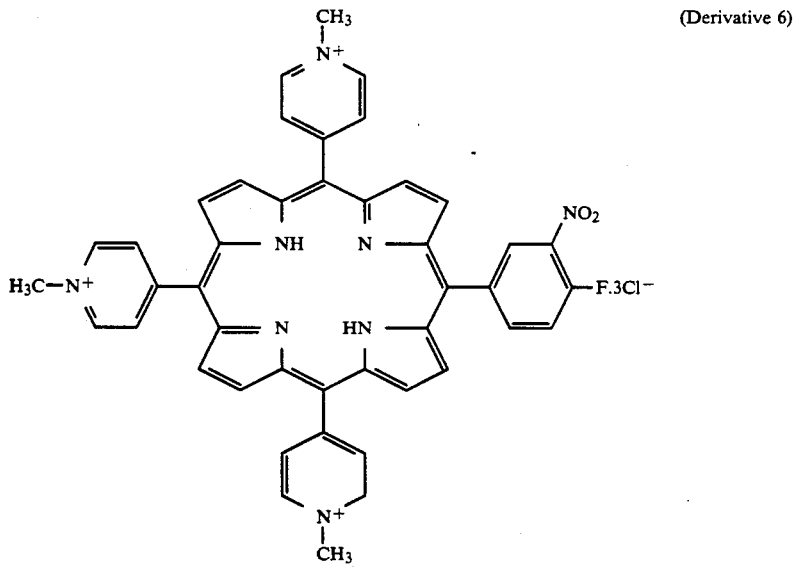

(Derivative 6)

$1.3 \cdot 10^{-4}$ mole of (3-nitro-4-fluorophenyl)-tripyridyl porphyrin obtained in example 1 are dissolved in 10 ml This derivative complies with the formula:

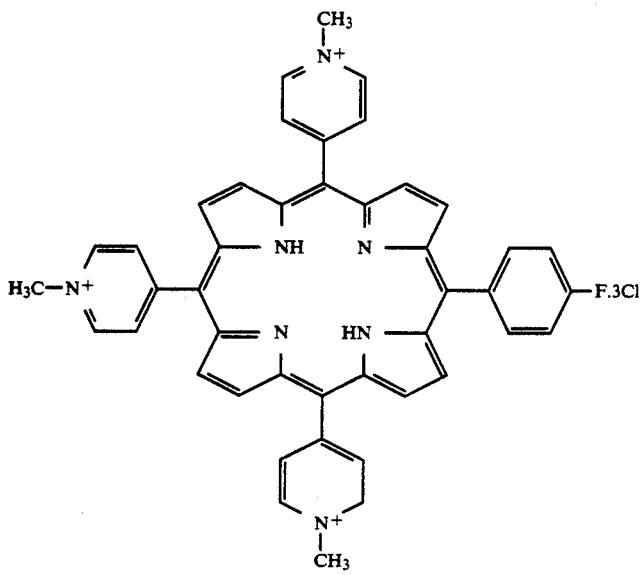

(Derivative 7)

The same operating procedure as in example 6 is followed, except that the starting product is $1.3 \cdot 10^{-4}$ mole of (4-fluorophenyl)-tripyridyl porphyrin obtained in example 2. This gives the chloride (derivative 7) with an 87% yield.

It has the following physicochemical characteristics:
Visible UV spectrometry (methanol), λ (in nm); 422; 514.5; 551; 589.5; 646.5.

$^1$H NMR (CD$_3$OD) δ(ppm): 9.11 (8H, m L); 9.39 (6H, d) 8.97 (6H, d); 8.18 (2H, m); 7.54 (2H, m); −2.90 (NH).

EXAMPLE 8

Preparation of (4-(carboxymethoxy)-phenyl)-trimethyl pyridylium porphyrin

This derivative complies with the formula:

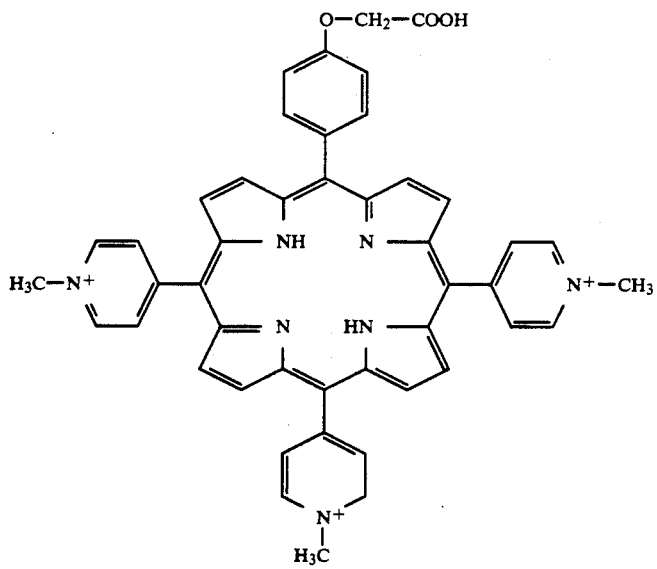

(Derivative 8)

The same operating procedure as in example 6 is adopted for preparing said chloride, except that the starting product is $1.3 \cdot 10^{-4}$ mole of (4-carboxymethoxy)-phenyl)-tripyridyl porphyrin obtained in example 4. This gives the chloride (derivative 8) with a 70% yield.

It has the following physicochemical characteristics:
Visible UV spectrometry (MeOH) (nm): 427.5; 518.5; 556; 592; 627.5.

$^1$H NMR (CD$_3$OD) δ(ppm): 9.05 (8H m, L); 9.37 (6H, d); 8.93 (6H, d); 8.09 (2H, m); 7.37 (2H, m); −2.96 (NH).

EXAMPLE 9

Preparation of indium ((3-nitro-4-fluoro)-phenyl)-trimethyl pyridylium porphyrin chloride (derivative 9)

In this example indium is inserted in the quaternized fluoroporphyrin obtained in example 6 using an isotopic indium mixture.

Evaporation to dryness under a nitrogen stream takes place of 1 mCi of indium trichloride in a hydrochloric acid solution. Following evaporation, addition takes place of $1.05 \cdot 10^{-7}$ mole of indium 115 trichloride and $1.40 \cdot 10^{-7}$ mole of quaternized porphyrin (derivative 6) of example 6 dissolved in an acetic-trifluoroacetic acid mixture (96.7 and 3.3%). The solution is refluxed (approximately 130° C.) for 3 h, accompanied by magnetic stirring.

The pH of the solution is adjusted to 4-5 by adding 1M soda. The product undergoes chromatography on an anionic resin and is recovered by 1 ml fraction. This gives the indium ((3-nitro-4-fluoro)-phenyl)-trimethyl pyridylium porphyrin chloride with a 75% yield.

EXAMPLE 10

Preparation of indium (4-fluoro-phenyl)-trimethyl pyridylium porphyrin chloride (derivative 10)

The same operating procedure as in example 9 is adopted, except that the starting product is porphyrin obtained in example 7 (derivative 7). Under these conditions the indium (4-fluorophenyl)-trimethyl pyridylium porphyrin chloride is obtained with an 85% yield.

EXAMPLE 11

Preparation of indium (4-(carboxymethoxy)-phenyl)-trimethyl pyridylium porphyrin chloride (derivative 11)

The same operating procedure as in example 9 is adopted, except that the starting product is the porphyrin of example 8 (derivative 8). This gives the indium (4(carboxymethoxy)-phenyl)-trimethyl pyridylium porphyrin chloride with an 87% yield.

EXAMPLE 12

Preparation of the 4-methyl mercaptophenyl ester of indium (4-(carboxymethoxy)-phenyl)-tripyridyl porphyrin (derivative 12)

Once again this example uses an isotopic indium mixture. Evaporation to dryness takes place under a nitrogen stream of 1 mCi of indium 111 trichloride in hydrochloric solution. When evaporation is at an end addition takes place of $1.05 \cdot 10^{-7}$ mole of indium 115 trichloride and $1.40 \cdot 10^{-7}$ mole of porphyrin of example 5 dissolved in a mixture of acetic and trifluoroacetic acid (96.7 and 3.3%). The solution is refluxed for 3 h, accompanied by magnetic stirring. When the reaction is ended, the pH is brought to 4-5 by adding 1 M soda. This is followed by the extraction of the metalloporphyrin by chloroformic extraction (2×10 ml) and the organic phase is recovered and evaporated.

This gives the 4-methyl mercaptophenyl ester of indium (4-(carboxymethoxy)-phenyl)-tripyridine porphyrin with a 53% yield. This yield is lower than in the case of the preceding porphyrins and confirms the instability of the ester in the acid medium.

EXAMPLE 13

Preparation of 4-methyl mercaptophenyl ester chloride of indium (4-(carboxymethoxy)-phenyl)-trimethyl pyridylium porphyrin (derivative 13)

Dissolving takes place in 5 ml of methyl iodide of $7 \cdot 10^{-8}$ mole of indium porphyrin obtained in example 12 and the reaction medium is heated to 40° C. for 2 h and accompanied by magnetic stirring. The excess methyl iodide is then evaporated, the quaternized porphyrin taken up by 2 ml of methanol and it undergoes chromatography on a chloride ion anionic exchange resin and is evaporated to dryness. The quaternized indium porphyrin is thus obtained with a 74% yield.

EXAMPLE 14

Preparation of yttrium acetyl acetate 4-(carboxymethoxy)-phenyl)-tripyridyl porphyrin (derivative 14)

In this example, yttrium is inserted in the porphyrin obtained in example 4 using an isotopic yttrium mixture. Evaporation takes place to dryness under a nitrogen stream of 1 mCi of yttrium tri(acetyl acetate) in hydrochloric solution. Following evaporation, addition takes place of $1.05 \cdot 10^{-7}$ mole of yttrium tri(acetyl acetate) and $1.40 \cdot 10^{-7}$ mole of porphyrin (derivative 4) of example 4 dissolved in trichlorobenzene. The solution is heated to 250° C. for 4 h and accompanied by magnetic stirring, which corresponds to the following reaction:

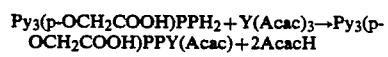

$$Py_3(p\text{-}OCH_2COOH)PPH_2 + Y(Acac)_3 \rightarrow Py_3(p\text{-}OCH_2COOH)PPY(Acac) + 2AcacH$$

in which Py=pyridyl, $PPH_2$=porphyrin in hydrogen form and Acac=acetyl acetate.

This gives yttrium acetyl acetate 4-(carboxymethoxy)-phenyl)-tripyridyl porphyrin with the following characteristics: Visible UV spectrometry ($CH_3OH$) λ (nm): 419 (Soret); 553; 593.

EXAMPLE 15

Preparation of yttrium acetyl acetate (4-(carboxymethoxy)-phenyl)-trimethyl pyridylium porphyrin chloride (derivative 15)

The yttrium porphyrin obtained in example 14 is quaternized adopting the same operating procedure as in example 6, reacting it with iodomethane and then subjecting it to chromatography on chloride ion anionic exchange resin. This gives the chloride, i.e. derivative 15, with a 75% yield and having the following characteristics: Visible UV spectrometry ($H_2O$) λ (nm): 431 (Soret); 558; 599.

Its stability in aqueous solution in contact with air and in the presence of light is very good, because the same visible UV spectra are obtained after 48 and 72 h, which clearly shows that this complex is very stable in the aqueous medium.

EXAMPLE 16

Preparation of a conjugate compound of indium (3-nitro-4-fluorophenyl)-trimethyl pyridylium porphyrin chloride and bovine serum albumin (BSA)

This example uses quaternized, metallized porphyrin obtained in example 9 and it is coupled with a biologically active molecule constituted by BSA.

$6.9 \cdot 10^{-8}$ mole of metallized porphyrin of example 9 are dissolved in 200 μl of water and 1 ml of 30% BSA is added to the water. It is left at ambient temperature and with stirring for 90 min, then undergoes chromatography on a 10 ml Sephadex ™ G75 gel column. The conjugate compound is recovered in 1 ml fractions between the 3rd and 8th fractions with a yield of 95%.

EXAMPLE 17

Preparation of the conjugate compound of indium 111 (4-fluorophenyl)-trimethyl pyridylium porphyrin chloride and BSA The same operating procedure as in example 16 is adopted, except that the starting product is the metallized porphyrin obtained in example 10. In this way the conjugate compound is obtained with a 97% yield.

EXAMPLE 18

Preparation of the conjugate compound of the 4-methyl mercapto phenyl ester chloride of indium 111 ((4-methoxycarboxy)-phenyl)-trimethyl pyridylium and BSA The same operating procedure as in example 16 is adopted, except that use is made of the porphyrin of example 13. This leads to the conjugate compound with a 67% yield.

EXAMPLE 19

Preparation of the conjugate compound of indium 111 ((4-methoxycarboxy)-phenyl)-trimethyl pyridylium porphyrin chloride and BSA $6.90 \cdot 10^{-8}$ mole of indium porphyrin obtained in example 11 are dissolved in 200 μl of water and to it is added 1 ml of 30% BSA in water. This is followed by the addition of $1.30 \cdot 10^{-5}$ mole of N-hydroxy succinimide and $1.30 \cdot 10^{-5}$ mole of ethyl dimethyl aminocarbodiimide. The reaction medium is left for 90 min and it then undergoes chromatography on a Sephadex G75 gel column, the conjugate compound being recovered in 1 ml fractions between the 3rd and 8th fractions, giving the compound with a 38% yield.

EXAMPLE 20

Preparation of a conjugate compound of indium (3-nitro-4-fluorophenyl)-trimethyl pyridylium porphyrin chloride and an antibody The antibody used is an anti ACE monoclonal antibody (carcinoembryonic anti-antigen). This antibody is directed against antigens expressed by colorectal tumours.

Into 1 ml of a 0.5M sodium bicarbonate solution are introduced $2.6 \cdot 10^{-2}$ μmole of antibody and $2.6 \cdot 10^{-2}$ μmole of the indium porphyrin obtained in example 9. After 12 h contact, the conjugate antibody-porphyrin compound undergoes chromatography on a Sephadex G100 gel column, previously saturated with human serum albumin (HSA). The conjugate compound is recovered in 1 ml fractions between the 4th and 7th fractions.

The coupling is verified by centrifuging on a membrane permitting the passage of molecules having a molar mass below 50,000. The coupling yield is 60%.

The immunoreactivity of the complex is equal to 45% and there are 10 porphyrins per antibody.

EXAMPLE 21

Preparation of a conjugate compound of the metallized porphyrin obtained in example 10 and an anti ACE monoclonal antibody The operating procedure of example 20 is followed and the corresponding conjugate compound with 10 porphyrins per antibody is obtained. The coupling yield is 75%.

EXAMPLE 22

Preparation of the conjugate compound of the 4-methyl mercaptophenyl ester chloride of indium (4-(carboxymethoxy)-phenyl)-trimethyl pyridylium porphyrin and the anti ACE antibody $12.5 \cdot 10^{-42}$ μmole of the porphyrin obtained in example 13 are added to $2.6 \cdot 10^{-2}$ μmole of the ACE antibody and then the volume is topped up to 1 ml by adding water (pH 6 to 7). After a contact time of 2 h, the porphyrin-antibody conjugate compound is purified by anionic phase chromatography and the coupling yield is 35%.

The stability of the conjugate compounds obtained in examples 20 to 22 is very good. Thus, after 48 h at ambient temperature, the measurement of the residual activity after further centrifuging on a "Centricon" membrane shows that the conjugate compounds are integrally retained.

We claim:

1. A porphyrin derivative according to formula:

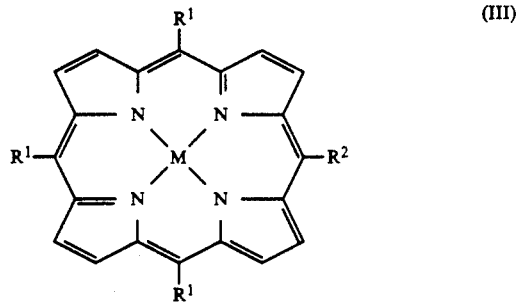

(III)

in which the $R^1$ represents a pyridyl group and $R^2$ is a group selected from the group consisting of the formula:

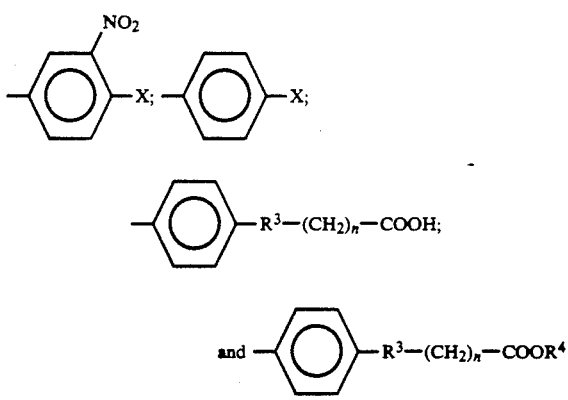

in which X represents F, Cl or Br, $R^3$ is a single bond, S or O, n is an integer from 1 to 7 and $R^4$ a $C_1$ to $C_4$ alkyl group, a benzyl group or a group of the formula:

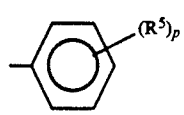

in which $R^5$ is F, Cl, Br, I, $NO_2$ or the group of formula $SR^6$ in which $R^6$ is a $C_1$ to $C_4$ alkyl group, p is equal to 1 when $R^5$ represents $NO_2$ or $SR^6$, or p is equal to 4 or 5 when $R^5$ represents F, Cl, Br or I, $R^5$ is in the ortho or para position when p is equal to 1 and M is a radioactive metal; and the pyridylium salts thereof.

2. A porphyrin derivative according to claim 1 in the form of its pyridylium salt of the formula:

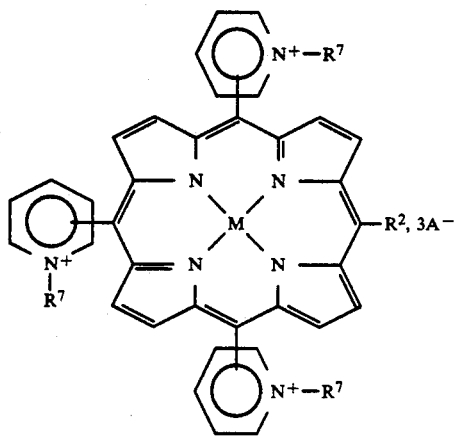
(IV)

in which $R^2$ is as defined in claim 1, $R^7$ is a $C_1$ to $C_4$ alkyl radical, A is an anion chosen from among $Cl^-$, $Br^-$ or $I^-$ and M is a radioactive metal.

3. A derivative according to claim 2, characterized in that $R^7$ is the ethyl or methyl group and A represents $Cl^-$.

4. A derivative according to claim 1, characterized in that M is a radioactive metal selected from the group consisting of indium, gadolinium, yttrium, rhenium, technetium, tin, gallium, copper, zinc and nickel.

5. A derivative according to claim 4, characterized in that M is indium 111, technetium 99m, rhenium 186 or rhenium 188.

6. A derivative according to claim 1, characterized in that $R^2$ is selected from the group consisting of:

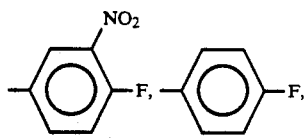

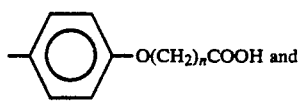

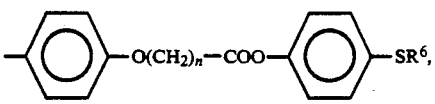

wherein n is an integer of from 1 to 7 and $R^6$ is $CH_3$ or $C_2H_5$.

7. A derivative according to claim 2, characterized in that M is a radioactive metal selected from the group consisting of indium, gadolinium, yttrium, rhenium, technetium, tin, gallium, copper, zinc and nickel.

8. A derivative according to claim 7, characterized in that M is indium 111, technetium 99m, rhenium 186 or rhenium 188.

9. A derivative according to claim 2, characterized in that $R^2$ is selected from the group consisting of:

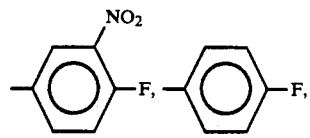

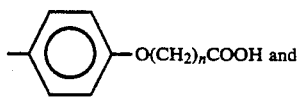

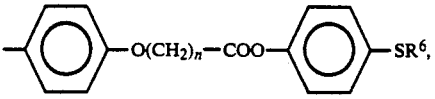

wherein n is an integer of from 1 to 7 and $R^6$ is $CH_3$ or $C_2H_5$.

10. A pharmaceutical composition, characterized in that it comprises, as active ingredient, a porphyrin derivative as defined in claim 1, in a pharmaceutically acceptable carrier.

11. A pharmaceutical composition, characterized in that it comprises, as active ingredient, a porphyrin derivative according to claim 2 in a pharmaceutically acceptable carrier.

* * * * *